(12) United States Patent
Ghodousi et al.

(10) Patent No.: US 9,435,744 B2
(45) Date of Patent: Sep. 6, 2016

(54) SAMPLE CARD SYSTEM AND METHOD FOR OPTICAL DETECTION USING CAPILLARY ACTION

(71) Applicant: REDXDEFENSE, LLC, Rockville, MD (US)

(72) Inventors: Arman Ghodousi, Alexandria, VA (US); Sarah Josepha Toal, Derwood, MD (US); Gregory Scott Ericksen, Silver Spring, MD (US); Daniel Douglas Montgomery, Washington, DC (US); Thomas Emory McVeigh, Lawrenceville, GA (US); Jacek Kotowicz, Washington, DC (US)

(73) Assignee: RedXDefense, LLC, Rockville, MD (US)

( * ) Notice: Subject to any disclaimer, the term of this patent is extended or adjusted under 35 U.S.C. 154(b) by 161 days.

(21) Appl. No.: 14/390,553

(22) PCT Filed: Apr. 3, 2013

(86) PCT No.: PCT/US2013/035121
§ 371 (c)(1),
(2) Date: Oct. 3, 2014

(87) PCT Pub. No.: WO2014/011261
PCT Pub. Date: Jan. 16, 2014

(65) Prior Publication Data
US 2015/0079693 A1 Mar. 19, 2015

Related U.S. Application Data

(60) Provisional application No. 61/619,674, filed on Apr. 3, 2012, provisional application No. 61/718,345, filed on Oct. 25, 2012.

(51) Int. Cl.
| | |
|---|---|
| G01N 21/62 | (2006.01) |
| G01N 21/00 | (2006.01) |
| G01N 21/78 | (2006.01) |
| G01N 21/84 | (2006.01) |
| G01N 33/22 | (2006.01) |
| G01N 15/06 | (2006.01) |
| G01N 15/00 | (2006.01) |

(52) U.S. Cl.
CPC .......... *G01N 21/78* (2013.01); *G01N 15/0612* (2013.01); *G01N 21/8483* (2013.01);

(Continued)

(58) Field of Classification Search
CPC ............. B01L 3/5027; B01L 2201/10; B01L 2300/0663; B01L 3/502715; B01L 3/50273; B01L 2400/06832; B01L 2200/16; B01L 2200/027; B01L 2300/0816; B01L 2400/0406; B01L 3/5023; B01L 3/502738; B01L 2300/08
See application file for complete search history.

(56) References Cited

U.S. PATENT DOCUMENTS 4,857,453 A * 8/1989 Ullman ............ G01N 33/54366
422/430

(Continued)

OTHER PUBLICATIONS

Halim et al., "*Analysis of Gunshot Residue Deposited on Cotton Cloth Target at Close Range Shooting Distances*", Malaysian Journal of Forensic Sciences, vol. 10, No. 1, pp. 48-53, 2010.

*Primary Examiner* — Yelena G Gakh
(74) *Attorney, Agent, or Firm* — Diederiks & Whitelaw, PLC (57) ABSTRACT

An analyte detection system and method for the detection of one or more analytes in a sample, the analytes selected from the group consisting of explosives, narcotics, gunshot residue, organophosphate reagents, and toxic industrial chemicals, based on a capillary action in a sample card. The sample card includes a housing with at least one cavity made of flexible material, a sample substrate for collecting the sample with a portion of the substrate exposed from outside the housing, at least one test capsule in the cavity and an absorbent pad. The test capsule(s), the sample substrate, and the absorbent pad comprise at least one or more reagents. The test capsule(s) is ruptured with a rupture mechanism upon inserting the sample card into a reader device. The absorbent pad absorbs a liquid from the test capsule and delivers the same to the sample substrate. The reagent(s) from any of the test capsule(s), the sample substrate, and the absorbent pad chemically react with the analyte(s) in the sample thus providing their optical detection. The sample card is automatically tested within the reader device which supplies one or more light sources, records and processes an optical signal produced by the chemical reaction, and outputs a test result.

18 Claims, 6 Drawing Sheets

(52) U.S. Cl.
CPC ....... *G01N33/22* (2013.01); *G01N 2015/0096* (2013.01); *G01N 2015/0693* (2013.01); *G01N 2201/062* (2013.01)

(56) References Cited

U.S. PATENT DOCUMENTS

| | | | |
|---|---|---|---|
| 5,096,669 A * | 3/1992 | Lauks | ............... B01L 3/502707 204/403.02 |
| 6,656,428 B1 | 12/2003 | Bickoff et al. | |
| 7,629,885 B2 | 12/2009 | Dugan et al. | |
| 2008/0145272 A1 | 6/2008 | Feaster et al. | |
| 2008/0199851 A1* | 8/2008 | Egan | ..................... B01L 3/5023 435/5 |
| 2010/0184229 A1* | 7/2010 | Haas | ..................... G01N 1/4022 436/50 |
| 2010/0190268 A1 | 7/2010 | Jina | |
| 2011/0236879 A1 | 9/2011 | Egan et al. | |
| 2012/0211088 A1 | 8/2012 | Nelson et al. | |

\* cited by examiner

SAMPLE CARD SYSTEM AND METHOD FOR OPTICAL DETECTION USING CAPILLARY ACTION

CROSS-REFERENCE TO RELATED APPLICATIONS

This application represents a National Stage application of PCT/US2013/035121 entitled "System and Method for Optical Detection Using Capillary Action" filed Apr. 3, 2013, pending which claims the benefit of U.S. Provisional Patent Application Ser. No. 61/619,674 entitled "Optical Capillary Action Test Kit", filed Apr. 3, 2012 and U.S. Provisional Patent Application Ser. No. 61/718,345, filed Oct. 25, 2012.

BACKGROUND OF THE INVENTION

The present invention pertains to the field of analyte detection and, more specifically, to an automated system and method for the use of fluorimetric and colorimetric detection inks and capillary action to detect one or more target analytes, including explosives, narcotics, organophosphates, gunshot residue and toxic industrial chemicals.

The detection of small amounts of explosives is important for the prevention of terrorist attacks and for the safeguarding of civilians, military personnel and bases, airports and other transportation locations, and tourist and commercial venues. The low volatility of many explosives, such as TNT, RDX, and PETN, makes vapor sampling difficult and largely inefficient, especially at low temperatures. Thus, efficient solid-state sampling techniques are desirable for many applications. Chemical sensors are often desired because they are able to detect trace amounts of explosives and can be packaged into simple-to-use, low-cost devices. Conventional detection methods, such as X-ray diffraction, nuclear quadrupole resonance, and gas chromatography-mass spectrometry, though highly sensitive, are expensive, difficult to maintain, susceptible to false-positives, and are not easily manufactured into low power, portable devices. Low end systems, while physically simple compared to the high end systems, require more complex user interaction and interpretation.

A major source of terrorist funding is gained through narcotics trafficking. This relationship implies that there could be a correlation between narcotics and terrorist weapons, including explosives. Therefore, the ability to detect narcotics concurrently with explosives may potentially be valuable in fighting the terrorist network at large. In addition to the international needs, narcotics detection is also a focus for other domestic criminal and forensic applications. Narcotics of particular interest are heroin, cocaine, marijuana, and methamphetamines. Analytical instrumentation, such as FT-IR, Raman, GC-MS, and IMS, may be used to identify specific drugs, but these are typically ill-suited for widespread field use because of their size and/or expense. Existing colorimetric detection technology employed in presumptive forensic field-test kits is used to detect visible quantities of narcotics that are typically low milligram quantities. Many of these kits require sampling and dispensing an amount of one or more solutions into a reservoir, visually interpreting a color change, and referencing a color chart to look for a specific color while discounting other colors. This process can be time consuming, subject to bias in an individual's perception of color. The overall performance is subject to change based on an individual's eye sight and external lighting conditions. Automating the detection of these colorimetric kits would at least remove the subjectivity in detection and performance dependency on external lighting conditions.

Like narcotics, gunshot residue (GSR) is an important analyte of interest for both domestic and international operations. Colorimetric kits exist for GSR detection, most of which rely on detection of post-blast nitrate and nitrite residue, and the signal degrades rapidly after firing. Field samples most often represent metal particles collected from a primer and sent to a lab for analysis, typically by a scanning electron microscope (SEM); results are often not available for weeks. A rapid and reliable field test would yield information immediately to assist law enforcement in their duties.

A multi-assay tool capable of detecting explosives, narcotics, and GSR in a single instrument and correlating this data would be a valuable tool in combating terrorist and criminal activities, both domestically and internationally. Optimization of such a tool for widespread use would require simplicity of use, portability, low power and maintenance requirements to be incorporated in a low cost device. Additional advantages would be gained by minimizing user interactions, particularly the number of analysis steps and ambiguity in user interpretation. Importantly, such an automated tool would allow for greater sensitivity and eliminated dependency on external lighting conditions and viewer's eyesight.

SUMMARY OF THE INVENTION

The present invention is directed to a product and method for the detection of one or more analytes in a collected sample, using capillary action in a sample card containing a sample substrate, which may have reagents embedded thereon, a test capsule containing a solvent reservoir and optionally containing detection reagents, and an absorbent pad that absorbs the contents of the test capsule and delivers the same to the sample substrate, and which may also have reagents embedded thereon, and a device which supplies one or more light sources, and records and processes the optical signal produced by the reaction between the detection reagents and the collected sample, and outputs a test result. The substrate may also contain a calibration signal to ensure the viability of the card and the validity of the test result. Additional aspects of the invention resides in the sample card itself, the use of the card with and without the reader device, visual analysis of the optical signal to determine a test result, and the specific form factor of the card itself.

The present invention is directed more specifically to the detection of one or more of the following analytes: explosives, including nitroaromatic-, nitramine-, organic nitrate-, inorganic nitrate-, chlorate, perchlorate-, bromate-, and peroxide-based explosives; narcotics, including cocaine, heroin and other opiate drugs, marijuana, synthetic marijuana (e.g. K2, spice), PCP, LSD, GHB, Cathinones (bath salts), and methamphetamines (including salts and free-base forms of all narcotics); organophosphates; gunshot residue; and even toxic industrial chemicals.

The sample card may also contain a key, such as a bar code, color code graphic or notch in the housing, to indicate to the device which test (e.g. explosives versus narcotic) is being run to minimize possibility of operator error, and enable optimized analysis methods specific to the substance or class of substances for which the user is searching. In addition, the sample card may contain a unique identifier, such as a bar code serial number or area on which to write specific information, to assist in chain of evidence handling.

The card may further contain a removable protective card cover over the sampling area to protect the reader device and sampling area from contamination before or after sampling, and to protect the user from touching the detection inks after the card has been processed.

Embodiments of the invention include the use of specific optical inks for the detection of explosives and narcotics. This includes their use in the present device, their use in the card component independent of the device, and other form factors. A test for PCP, methamphetamines, amphetamines, and cathinones, MDPV, mephedrone, mescaline, 2C-I and pyrovalerone, and their structurally related compounds and salts is disclosed which uses a pyrylium salt in an aqueous organic solution. A preferred embodiment of the methamphetamine and amphetamine test uses the ink on a substrate with a base, such as sodium hydrogen carbonate, sodium phosphate, sodium carbonate, or hydroxide salts contained thereon. A test for nitramine and organic and inorganic nitrates is also disclosed using a reducing agent and an organic amine in an acidic medium. A test for peroxide, chlorate, and bromate explosives is disclosed using an azino compound and an acid. A test for opiate-containing analytes using cis-aconitic anhydride is disclosed, preferably using an acid. A test for detecting and distinguishing between cocaine and PCP is disclosed, using both a cobalt(II) salt and a pyrylium salt, wherein the compounds may be distinguished based on the difference in color that results when the salts react with the drugs.

Additional objects, features and advantages of the invention will become more readily apparent from a detailed description of preferred embodiments thereof with reference to the drawings wherein like reference numerals refer to corresponding parts in the several views.

DETAILED DESCRIPTION OF THE INVENTION

The present invention is aimed at an analysis test for the detection of small amounts of analytes that may be present on a surface, which uses a liquid and capillary action to deliver reagents to a sample. In general, the test uses a sample card and a reader device. The sample card comprises a housing, a substrate for collection of a suspect material, one or more test capsules containing a liquid to react with the suspect material, and an absorbent pad to receive the liquid and to allow it to wick up the substrate in a controlled manner. The substrate and/or absorbent pad may optionally contain embedded reagents to react with the collected sample or liquid in the test capsule. A sample collection aid may optionally be used to acquire and/or transfer the suspect material more efficiently. The sample card contains an identifying mark, such as a bar code or notch in the housing, to indicate to the device the type of card being used. The reader device contains a housing with an input location (card carrier) to receive the sample card, a rupturing mechanism to break the test capsule, an internal light assembly to illuminate the sample and/or to initiate a reaction between the suspect material and reagents, solvent and/or solution, to produce an optical signal. The reader device also contains an optical reader to observe and record an optical signal, a signal processor to analyze the signal or recorded signal (a digital image of the signal) and determine a test result, and a means for communicating the test result to an operator.

Figure 1:
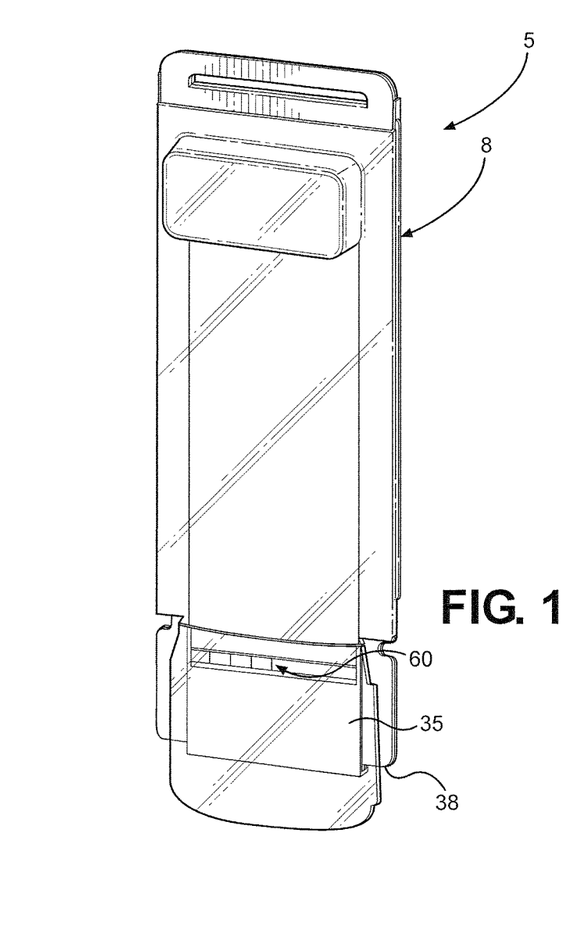
FIG. 1 is a perspective view from one side of a sample card employed in the optical detection device of the invention.
Figure 2:
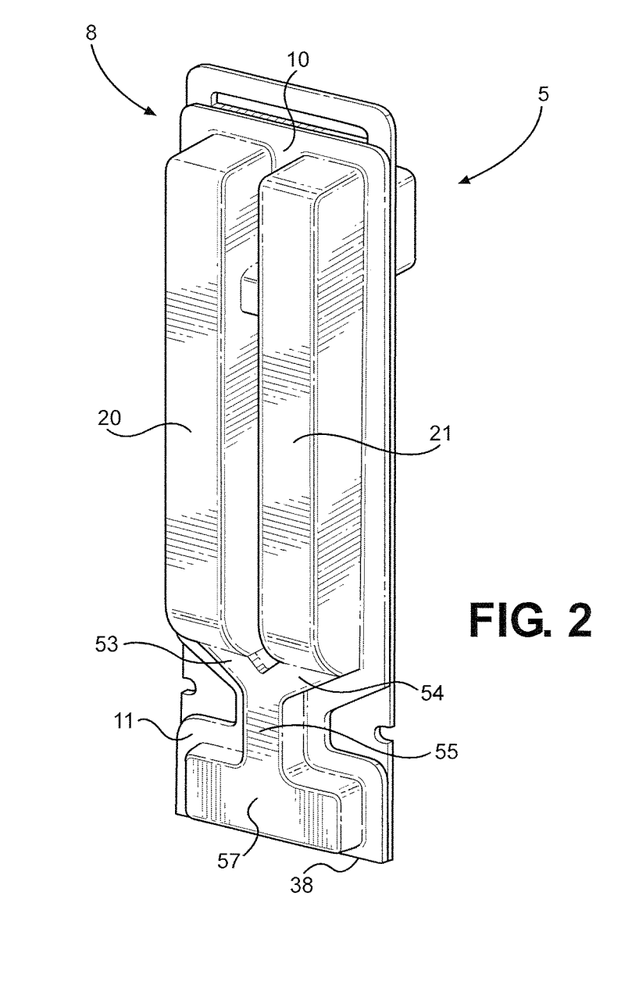
FIG. 2 is a perspective view from another side of the sample card of FIG. 1.
Figure 3:
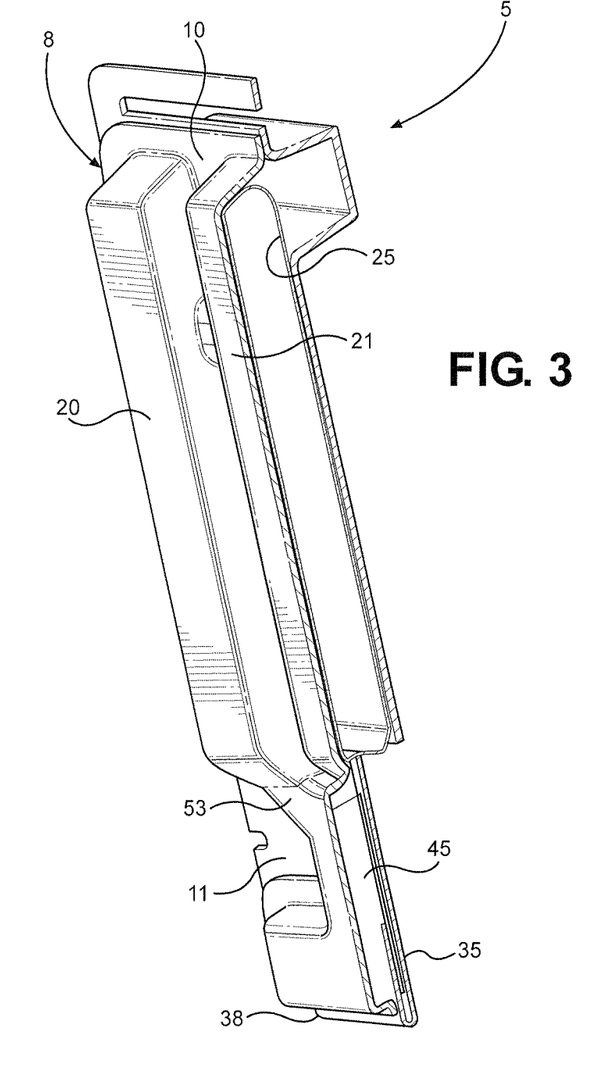
FIG. 3 presents a cross-sectional view of the sample card.

In describing exemplary embodiments of the invention, reference will initially be made to FIGS. 1-3 in describing the sample card which is generally indicated at 5. As illustrated, sample card 5 includes an outer covering or housing 8 which contains the other components of the sample card. Housing 8 includes an upper housing portion 10 and a lower housing portion 11. Housing 8 is preferably made of plastic or Teflon, but may be made of other materials. The housing 8 is formed with one or more cavities, with the illustrated embodiment depicting two such cavities 20 and 21, each of which is designed to hold a respective test capsule 25 shown in the form of an ampoule. Card 5 also holds a sample substrate 35, such as a paper substrate, for sample collection, with sample substrate 35 being shown exposed on or near a bottom edge 38 of sample card 5. Also provided as part of sample card 5 is an absorbent pad 45 which is positioned adjacent cavities 20 and 21 and juxtapose sample substrate 35.

Housing 8 is made of a flexible material which is compliant when pressure is applied. With this arrangement, as will be detailed more fully below, applying pressure to housing 8 at cavities 20 and 21 will cause the associated capsules 25 to burst such that liquid, e.g., a solvent with detection reagents, contained in the ampoules will be directed onto absorbent pad 45. In one embodiment, channels, such as shown at 53 and 54 in FIG. 2, can be formed as part of housing 8, with each channel leading from a respective cavity 20, 21. As shown, channels 53 and 54 merge at 55 above a reservoir 57. When multiple test capsules are employed, merging of the channels 53 and 54 allows solutions from the multiple cavities 20 and 21 to mix before coming into contact with or within the absorbent pad 45. This arrangement allows storage of incompatible solutions in the different capsules or ampoules 25, while accommodating mixing of the solutions to establish a testing solution prior to reaching the absorbent pad. In other embodiments, the solutions from the capsules 25 do not mix, but rather travel down to separate absorbent pads (not shown). In either case, from the absorbent pad 45, the testing solution wicks up the paper substrate 35 either along a common portion of the substrate 35 or along two different portions of the substrate 35. In the latter case, two detection tests can be run in distinct areas of the card to either test for two different materials, for false alarm mitigation, or to allow an internal calibration or control area.

At this point, it should be noted that the substrate 35 used to collect a sample of a suspect material allows the solution(s) contained in the capsules 25 to migrate along its surface and react with the sample, producing an optical signal. That is, each capsule 25 contains a solvent that is chosen and/or formulated to dissolve the suspect material and other detection reagents in the sample card 5 and facilitate a reaction between them to produce an optical signal, i.e. a fluorimetric or colorimetric signal. The substrate 35 may also contain embedded reagents that further react with the solvent/solution in the capsules and/or the suspect material. The substrate 35 may be cellulose paper, glass fiber paper, cotton paper, or other material such as a cloth or muslin material that acts as a wick to absorb the solution and allow capillary action to draw the solution up the length of the substrate 35. In the embodiment shown, the paper wraps around the front of sample card 5. One end of the paper is placed between the housing 8 and the absorbent pad 45, and folded around the front of the housing 8. The paper may be held down by an adhesive label (shown without a reference numeral), which may also contain marketing and/or other information as to which analytes may be detected with the particular sample card 5. The exposed portion of the paper is the sample collection area. Swiping or dragging the paper along a surface is a convenient method of collecting a sample. Once the liquid is released from the capsule(s) 25, it will dissolve any reagents embedded on the absorbent pad 45 and substrate 35 and wick along the substrate 35. Therefore, a wicking material and capillary action is employed to deliver a liquid to a test area and create an optical signal, usually a calorimetric signal, to indicate the presence of a specific analyte. The simplicity of this design approach is useful for determining the presence of compounds that require a single detection solution, or can be performed in a single step by carrying solution to a solid reagent embedded in the solvent wicking pathway. The arrangement is considered particularly useful when solid particulates must be extracted from a sample to avoid interference in the detection signal.

In any case, as the solution passes through the sample, the target analyte is dissolved and carried along the length of the substrate 35, and produces an optical signal. Users may be directed to sampling on the bottom edge so that as the ink (solution) passes over the substrate, dirt and other large particles are left at the bottom of the sample collection area and are positioned such that they can be removed or otherwise excluded from the signal processing. A sample collection aide may also be used in conjunction with the sample card 5 to make sampling from certain surfaces more efficient. For example, a cotton swab may be used to collect a sample from the inside of a small bag and then rubbed on the sample collection area of the paper. In other embodiments, the substrate preferably has a portion which is not used for sample collection and serves as a control area. This portion may contain a small amount of material which will generate the target signal to assist signal processing and to ensure that each card is performing properly.

The sample card 5 may also be designed with an identifying indicator or mark 60, such as in the form of a mechanical key, bar code, notch or other physical or graphical component, located on the housing 8, the substrate 35, or a label (not shown) affixed to sample card 5. Identifying indicator 60 functions to specify the type of sample card 5 and, correspondingly, the solution/substrate contained therein such that the appropriate sample card 5 can be employed for a given test, e.g., a cocaine test vs. a homemade explosive test. The identifying indicator 60 can be employed for visual identification with the human eye, or recognized by an optical reader or camera. In any event, the identifying indicator 60 correlates with the type of test being performed. In certain embodiments of the invention, the inclusion of the identifying indicator 60 allows the overall system to automatically determine and perform the desired testing with the appropriate sensing algorithms, processing and analysis. Sample card 5 may also have an area on which to write notes to allow sample card 5 to be used for evidentiary purposes.

Figure 4:
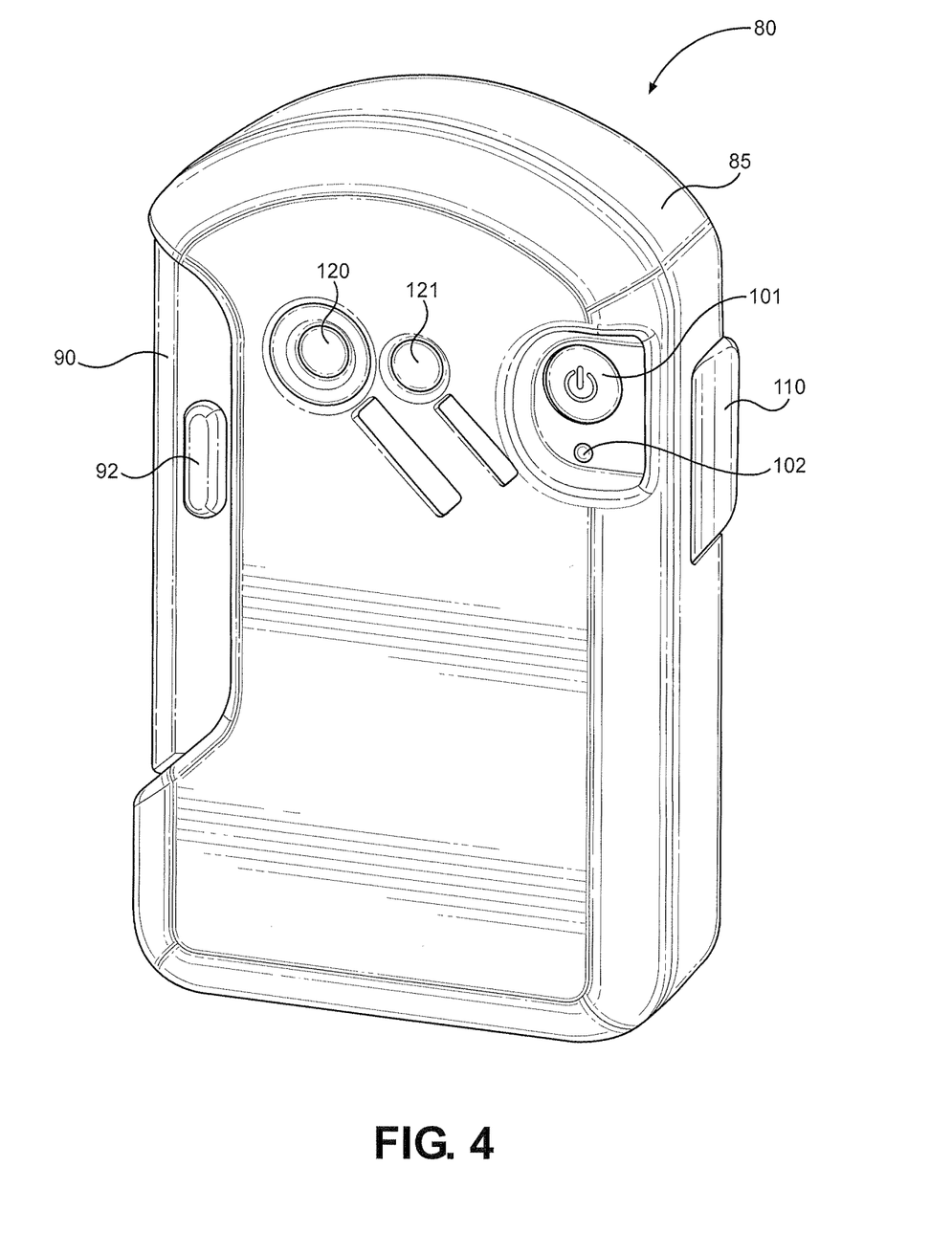
FIG. 4 is a perspective view of a reader of the optical detection device shown in a closed condition.

In accordance with the invention, sample card 5 may be used independently, with the optical signal being observed visually by the user to determine a test result. More preferably, the card 5 is used in conjunction with a reader device 80 to determine the test results automatically, as will now be detailed with reference to FIGS. 4-6. As shown, reader device 80 includes a main housing 85 having a door 90 which can be pivoted or otherwise shifted between opened and closed positions, with the opened position being achieved through activation of a release button 92. Reader device 80 also includes a power button 101 and an activation and/or low battery indicator light 102. Also shown provided on a side of main housing 85 is a port cover 110, such as a rubber insert, which can be selectively removed to expose an area for connecting reader device 80 to an electrical outlet for charging purposes, connecting reader device 80 to a computer via USB or other communication port for data storage/transfer and firmware upgrading purposes, and inserting/removing a memory card (not shown). Furthermore, reader device 80 includes one or more communication ports, such as indicated at 120 and 121. In this embodiment depicted, each communication port 120, 121 contains an LED light, e.g., a green light and a red light, used to respectively convey positive and negative results of a given test.

Figure 5:
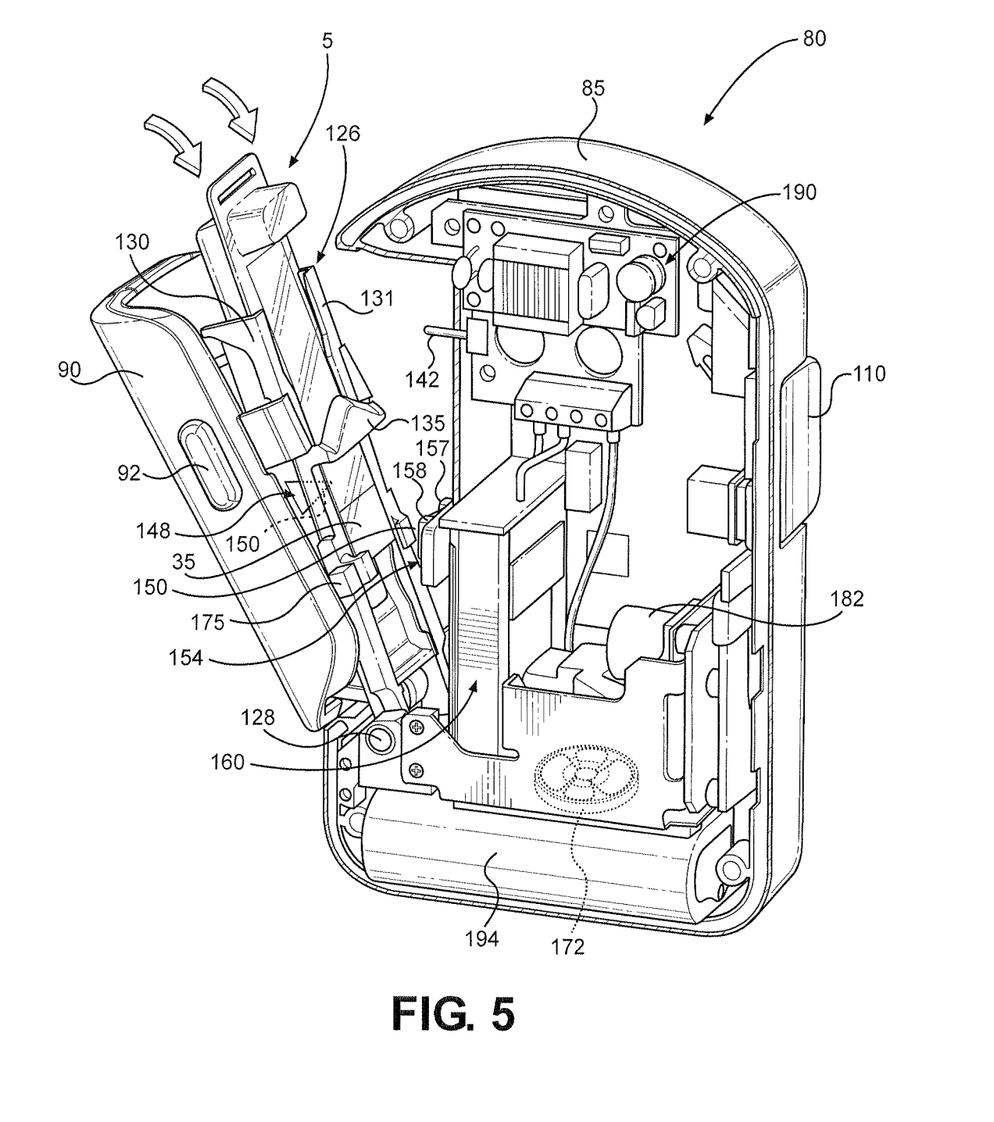
FIG. 5 illustrates the reader of FIG. 4 in an open condition and with internal components being depicted.
Figure 6:
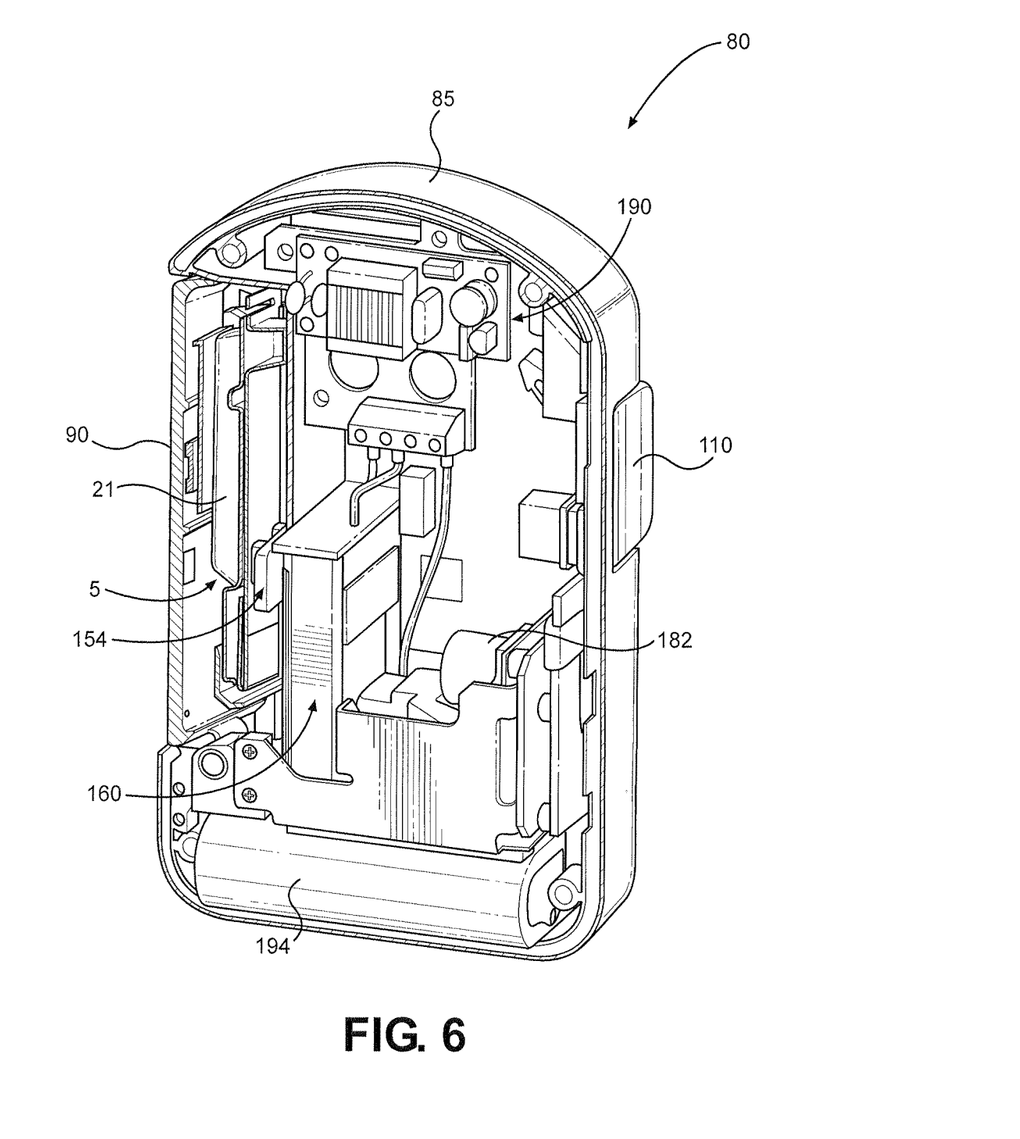
FIG. 6 is a view similar to FIG. 5 but with the device in the closed condition.

Reader device 80 also includes various internal components as shown best in FIGS. 5 and 6. More specifically, reader device 80 has a card carrier 126 into which the sample card 5 is placed for testing purposes. The card carrier 126 is shown extending into an inside portion of door 90 and is separately, pivotally connected to main housing 85 for movement about a pivot axis 128, but could take other forms, such as a slot or a sleeve that is exposed when a door is opened. As illustrated, card carrier 126 includes side guide channel members 130 and 131 which are interconnected by a crosspiece 135. Sample card 5 is configured to fit between side guide channel members 130 and 131, and behind crosspiece 135. Proper positioning of sample card 5 contributes in minimizing cross-contamination between the sample collection area and the reader device 80. With this arrangement, when door 90 is opened, the card carrier 126 pivots out as shown in FIGS. 5 and 6 so that card carrier 126 is readily accessible by an operator for inserting or removing of sample card 5. The reader device 80 may contain a card sensor, which senses when a sample card 5 is fully engaged in card carrier 126. The device may also contain a door sensor, which senses when door 90 is fully closed. Preferably, the card and door sensors is constituted by a single mechanical switch 142 which senses when both a sample card 5 is inserted in card carrier 126 and door 90 is closed. Preferably a detection cycle is automatically started when the sensor 142 determines the sample card 5 has been inserted and the door 90 has been subsequently placed in the closed position which, in the embodiment shown, also constitutes pivoting door 90 about axis 128. If door 90 is open during a detection cycle, the system would abort the current detection process, such as to assure an accurate analysis and to protect the user.

The reader device contains a rupture mechanism generally indicated at 148. Basically, rupture mechanism 148 functions to rupture the capsules 25 or otherwise releases their liquid, typically by applying pressure to or puncturing the capsules. Pressure can cause glass or plastic ampoules to break, or a plastic pouch to burst and release its contents. In the depicted embodiment, door 90 on main housing 85 is provided with a protrusion 150 which extends into the card carrier 126 when door 90 is closed. More specifically, main housing 85 has mounted therein an anvil member 154 which is shown to include two support blocks 157 and 158 which align with cavities 20 and 21. When door 90 is closed, cavities 20 and 21 are limited in movement based on the presence of blocks 157 and 158 while protrusion 150 pushes against capsules 25, thereby rupturing capsules 25 and releasing their contents. When the door 90 is opened, the protrusion 150 is pulled out from the card carrier 126, allowing one sample card 5 to be removed and another inserted and fully coupled to card carrier 126. Another embodiment allows two or more capsules to be broken at different times, thus allowing a time-release or multiple-ink detection process to take place. Once the contents are released, they funnel down to the absorbent pad 45. Upon wetting, the solution is drawn from absorbent pad 45 to and along the substrate 35 through capillary action. It passes through the sample collection area and the collected sample.

Reader device 80 can also have a means to sense indicator 60 to determine the specific analyte or group of analytes of interest for which the sample card 5 has been designed. Reader device 80 can therefore execute a predetermined protocol specific to the individual sample card 5. For example, different lighting and signal processing, heating and drying cycles may be used for nitroaromatic explosives than for specific narcotics. As referenced above, this sensing may be done by reading and analyzing various different indicators, including a bar code, color code graphic, or other printed graphical code on the label or a physical key on sample card 5.

The reader device 80 also contains a light assembly 160, which may serve multiple purposes. In particular, light assembly 160 illuminates the sample such that an optical reader (discussed further below) can determine the sample card type (e.g., by illuminating the identifying mark 60), verify the status of the solvent flow (e.g. ensure the sample card 5 is not defective), and read the optical signal caused by the interaction of the solution and the collected sample. The light assembly 160 may also further serve to initiate or stimulate a reaction. The light assembly 160 may be comprised of one or more light sources, including white light, UV light, and infrared light. This may be supplied by light emitting diodes (LEDs), cold cathode fluorescent lamps (CCFLs), or hot cathode fluorescent lamps (HCFLs). The light assembly 160 also illuminates an optical signal. For colorimetric signals in the visible spectrum, white light may be used; for fluorimetric signals, UVA or UVB light may be shone onto the sample to stimulate the optical signal. There may also be a portion of the substrate 35 that is not exposed to the suspect material which serves as a control. This portion of the substrate 35 will show an optical signal from the solution itself as it would appear if it had not come into contact with the target material for which it was formulated to detect.

Reader device 80 may optionally include a fan 172 to help dry the solvent from the viewing area if necessary. The reader device 80 may also include a heater 175 to aid in drying or to stimulate a reaction between the sample and solution, depending on the specific chemistry related to the card. The convection flow or heat may be triggered automatically when reader device 80 senses the solvent front has reached a specific point in the viewing window. In another manner, the function of the convection flow and heat may be controlled in a time sequence after initiation of a detection process based on the individual card type.

Reader device also contains an optical reader 182 to observe and record an optical signal from the substrate 35, i.e., both the portion which is exposed to the sample, and the control area, if included. Optical reader 182 can take various forms, but preferably takes the form of a simple camera or spectroscopic reader. Preferably optical reader 182 records a digital image of the sample collection area and the optical signal. Furthermore, several images may be captured and recorded in a timed sequence and analyzed for changes in the optical signal from one image to the next, thereby identifying and incorporating attributes that evolve over time, and allowing a test result to be determined as soon as possible to minimize overall detection time.

Reader device 80 further contains a signal processor or controller 190 which is powered by a rechargeable battery 194 and has the capability to aggregate data from multiple sensor inputs and determine a test result. Various inputs can be collected, including temperature and humidity signals from sensors (not shown) within housing 85. More specifically, controller 190 includes an image processing capability to assess the optical signal as recorded in a digital image from the processed sample for the presence of the target analyte. The image processing may include preprocessing such as the collection of a preprocessed image, masking of preexisting signals, and normalization. In the preferred embodiment, the image processing includes multiple orthogonal attributes of the optical signal to produce a robust and reliable assessment. The assessment attributes may include color component identification and/or separation, signal energy levels, relationships between color components, time domain appearance and disappearance of signals, signal shape, and signal distinction. Color component identification may include pre-determined acceptable color component range variations for each component (e.g. red-blue-green (RGB) components or hue-saturation-brightness (HSB) components), and a logical test to determine if the interrogated color point falls within the acceptable range variations for each component. In one embodiment, a control signal may be embedded and processed on the same sample card 5 used to collect the suspect material. In another embodiment, the control signal may be collected in advance and independent of the sample collection and analysis process. In addition to the digital image, additional sensor inputs evaluated by the signal processing capability may include temperature and humidity measurements, which may affect the parameters by which the optical signal is assessed. The extracted assessment attributes are compared to the control signals and an overall assessment regarding the presence of the target analyte is made (i.e. the unit determines a test result).

For sample cards that have two capsules whose contents do not mix before reaching a sample paper, but rather travel side-by-side to the sample collection area, the signal processing compares the two optical signals to determine the test result. This may be used as a means to mitigate false alarm or to improve the specificity of the test. For instance, one capsule may be used to test for the presence of either cocaine or PCP while the other side would test for PCP only. If both sides produce a positive signal, the signal processor would determine a positive test result for PCP; if only one side produces a positive signal, the device would determine a positive test result for cocaine.

The test result is communicated to the user through a communication system, such as by providing an indication of either a 'detection' or 'not a detection'. Preferably, the communication system may also communicate an error to the user. Such instances warranting an error message would be to indicate a defective card (e.g. no solvent front was detected after an analysis started) and to indicate a card not supported by the unit's currently installed firmware is present (e.g. the unit was unable to read the unique identifying mark). The communication system may include LEDs, an LCD display, or other audio, visual or vibration cues to the user regarding the status of the device and the test result. In one embodiment, two LEDs are provided at communication ports 120 and 121 as detection indicators to indicate a positive detection or no detection. Preferably multi-colored LEDs are used such that error messages may be communicated through different colors than the detection/no detection colors. In another embodiment, an LCD display may give textual and/or pictorial commands.

Preferably, reader device 80 further contains data storage and communications capabilities. That is, the images captured from optical reader 182 may be stored, as can intermediate results and final results from the optical signal analysis. This stored information may be communicated to the user for collection and storage with other forensic elements of the detection event. Reader device 80 may further support remote or local connectivity to allow data transfer.

Figure 7:
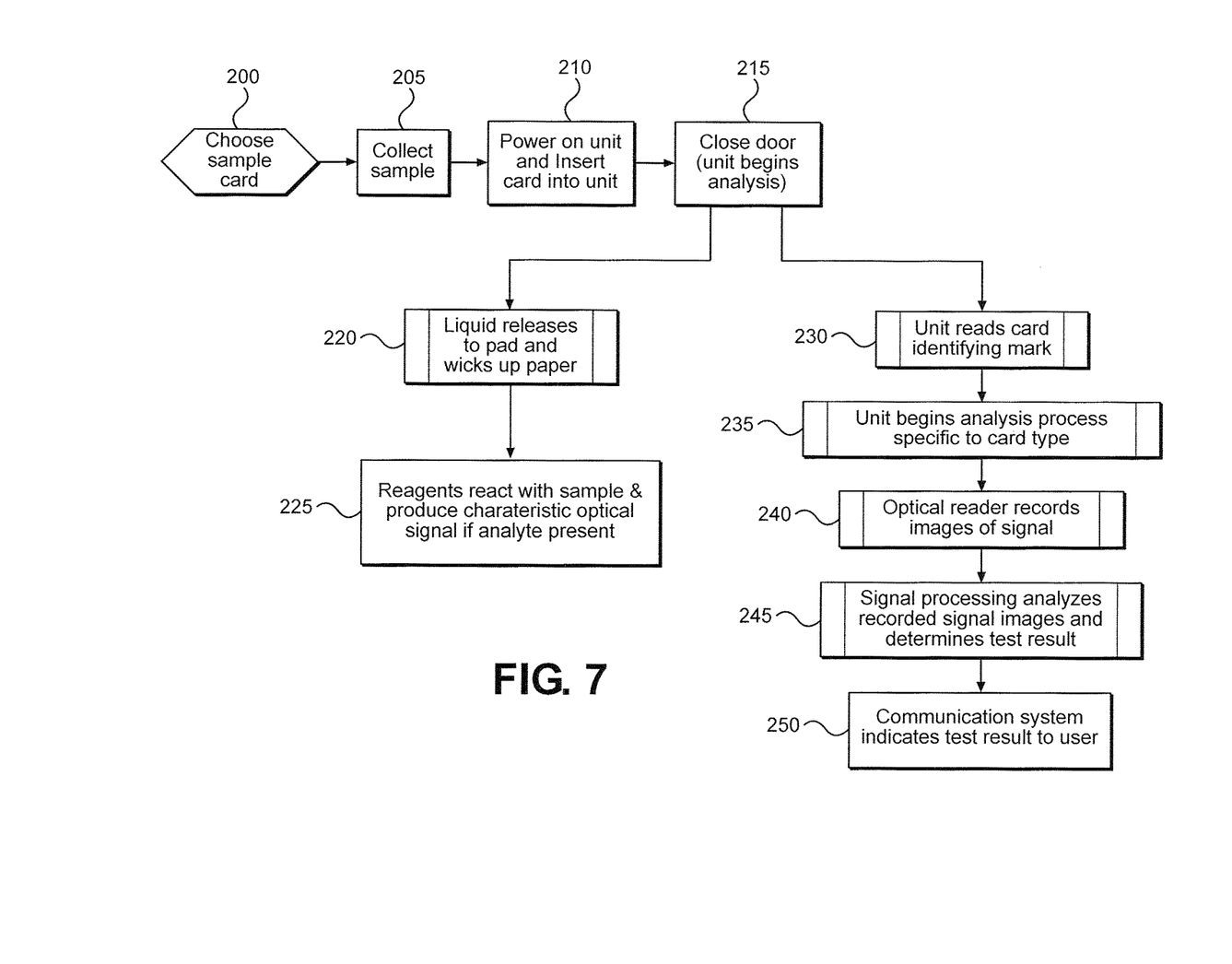
FIG. 7 is a flow chart outlining method aspects of the invention.

Reference will now be made to FIG. 7 in describing a typical analysis in accordance with the invention, with the typical analysis including a sample collection with sample care 5 and then analysis in reader device 80. First, an operator finds a sample to be tested. This may be a suspect powder (e.g. for a drug analysis), a suspect's hands (e.g. to determine if the suspect recently fired a weapon or has handled explosives), or other surface. The operator locates the correct sample card 5, specific to the analyte (e.g. heroin) or class of analytes (e.g. opiates) for the desired test as indicated at step 200. The surface on which the sample is present is then swiped at 205 with the sample collection area, or a cotton swab or other sample collection aide is wiped across the surface and the sample is then transferred onto the sample collection area. At step 210, the power to reader device 80 is turned on, door 90 is opened, and the sample card 5 is placed in card carrier 126, thereby coupling the sample card 5 to reader device 80. The door 90 is shut at 215, with one or more sensors 142 verifying that sample card 5 is present and door 90 is shut. With the shutting of door 90 on card 5, rupture mechanism 148 is engaged, causing capsules 25 to release their contents and the solvent to wick up the substrate 35 at step 220. As the liquid is released at 220 and the reagents react with the collected sample at 225, reader device 80 also begins to automatically initiate a detection cycle, including beginning with the system turning on white light to read an identifying mark on the card to determine which card is present at 230. The contents of the capsules 25 flow down the channels 53 and 54 to the absorbent pad 45. The absorbent pad 45 is in contact with the substrate 35, and allows the liquid to wick along the substrate 35 in a controlled manner through capillary action, which is in contact with the absorbent pad 45. If reagents are present on the pad or paper, the solvent dissolves them and carries them up the paper as well. The solution mixes with and reacts with the collected sample (step 225). White light is turned on and an optical reader 182 senses the presence of the solvent front and continues analysis (note, if no solvent was detected the system would return an error indicating a defective card). The system then optionally triggers, depending on a program defined by the specific sample card used, activation of drying fan 172 and/or heater 175 to dry the surface and potentially supply energy to increase the reaction rate. Lights are turned on, again specific to the individual sample card 5 used (step 235), and optical reader 182 records an optical signal (step 240). Signal processing system 190 analyzes the optical signal against a control area on the sample card and/or to pre-programmed color sets specific for the individual sample card 5. The signal processing system 190 determines a test result (step 245) and communicates it to the user (step 250) by lighting an LED to indicate the presence or absence of the suspect material.

The system described above holds significant advantages over current colorimetric detection technology available. For instance, the system provides magnification and high resolution, allowing for enhanced sensitivity, and need not be dependent upon an operator's eyesight or varying lighting conditions. It provides consistent interpretation of the detection result not based on personal bias, color variation, or perceptions of a user. The housing of the reader device chamber minimizes contamination, provides a controlled environment for the chemicals (e.g. temp, moisture, heating, drying) and increases safety. The automated system further allows the user to focus on his/her primary duty and provides detection consistency and accuracy that makes it suitable for presumptive tests used in legal cases.

In further accordance with the invention, there have been developed particular inks for use as the detection reagents for specified analytes. To this end, a new optical test solution for PCP, methamphetamines, amphetamines, and "bath salts" using a pyrylium salt is disclosed. This solution may be used in multiple form factors, including in the sample card disclosed herein. An optimal solution uses triphenylpyrylium tetrafluoroborate in an acetone:water mixture. Amphetamines, methamphetamines and their structurally-related compounds turn yellow or orange when exposed to this ink. PCP turns red or violet-red when exposed to this ink. To increase the sensitivity to the hydrochloride salts of the methamphetamines and amphetamines, a base may be added to the substrate or to the solution. The base deprotonates the narcotics, which allows them to react with the pyrylium reagent more efficiently. Useful bases include hydroxides, carbonates, phosphates, and bicarbonates. In a preferred embodiment, a PCP sample card uses a standard paper that has not been exposed to base. In a preferred embodiment, an amphetamines (and related compounds) sample card will test for the free-base and protonated forms, and will use a paper or absorbent pad that has been coated with a sodium bicarbonate prior to manufacturing of the sample card. Removing the base from the pyrylium solution in the test capsule improves stability of the solution. The yellow-orange to orange-red color produced by the reaction may be observed visually or in an automated system, such as the reader device described above.

In connection with an optical test for nitramines (e.g. RDX, HMX, C4), organic nitrates (e.g. PETN, Semtex, EGDN, nitrocellulose, nitroglycerin), and inorganic nitrates (e.g. ammonium nitrate, ANFO, urea nitrate, potassium nitrate, sodium nitrate), the detection reagents includes an acid, one or more organic amines, and a reducing agent. Preferably, the reducing agent is separated from the other compounds to ensure the stability of all compounds. In a preferred embodiment, a sample collection paper contains a reducing agent, preferably zinc dust, thereon. The paper is used to collect a sample and then exposed to an organic solution containing an acid, preferably hydrochloric acid, and one or more organic amines, and preferably at least N-(1-naphthyl)ethylenediamine. The reaction produces a strong pink color in the presence of these nitro-containing compounds. The pink color may be observed visually or in an automated system, such as the reader device described above.

A particular optical test for peroxide-, chlorate-, and bromate-containing compounds, including explosive-related compounds, is disclosed that uses an azino compound in an organic solvent containing an acid. Preferably, 2,2'-azino-bis(3-ethylbenzothiazoline-6-sulfonic acid) is used in a solution of ethanol and hydrochloric acid. Heat may be used to increase the reaction rate and efficiency. The reaction produces a green compound, which may be observed visually or instrumentally, such as with the reader device described above.

In an optical test for the detection of opiate compounds and cocaine, cis-aconitic anhydride in an organic solvent containing an acid, preferably acetic acid, is employed as the detection reagent. The reaction produces a yellow colored compound which may be observed visually or instrumentally, such as with the reader device described above.

An optical test for the detection and discrimination between cocaine and PCP is disclosed which uses a cobalt (II) salt and a pyrylium salt. Cobalt(II) compounds, particularly cobalt(II) thiocyanate, or Scott's reagent has long been used to detect cocaine through production of a blue compound. PCP is also detected with this reagent, though typically PCP has been described as a nuisance alarm for the tests marketed for cocaine detection. Addition of a pyrylium salt, preferably triphenylpyrylium tetrafluoroborate, causes the colored product of the PCP-product to shift from the typical blue color to a more green color. Thus, for a mixture of Scott's reagent and the pyrylium compound reacting with an unknown substance, cocaine can be assumed to be the analyte present if a blue color is observed, while PCP can be assumed to be the analyte present if a green color is observed. The color change and discrimination between the drugs may be observed visually or instrumentally, such as with the reader device described above.

Based on the above, it should be readily apparent that the system and method of the invention provides an efficient and effective arrangement for optically detecting one or more target analytes through capillary action. The device is simple to use wherein, in general, a person need merely collect a sample by swiping the swipe area on a surface, such as someone's hand, and then puts the card into the card carrier. Thereafter, the liquid containing ampoule within the card, which contains the ink solution, is crushed when a door to the optical reader device is closed. This causes ink to pass to the absorbent pad, which distributes a flow of ink to the chromatography paper on the swipe area. The ink then wicks up through the sample paper to the viewing window carrying the sample with it. The ink will dissolve explosives/narcotics/gunshot residue or other analytes and continue to pass to the viewing area on the other side of the card, while dirt and other contaminants do not enter the viewing area, thus simplifying the viewing analysis. White light is applied to the viewing area to determine when the ink hits a particular point, triggering a fan to be activated to dry the ink. Next an ultraviolet light is applied to the viewing area and a camera images the viewing area, sending a signal to a computer processor which has software used to analyze the signal based on the sensing of an identifying mark provided on the card which sets the analysis protocol. The system then outputs either an indication that an analyte has been found or has not been found. Preferably the signal sent by the camera is a fluorimetric or colorimetric signal, but also could incorporate spatial analysis looking for streaks that are often present in nitrate explosives. Overall, a user need only turn the power on, put a sample containing card in the reader device, subsequently close the door, and wait for a red or green light to indicate whether or not contraband is present.

Although described with reference to exemplary embodiments of the invention, it should be understood that various changes and/or modifications can be made to the invention without departing from the spirit thereof. For instance, the sample card may have a cap or protective cover (shown but not labeled), which is completely or partially removable, to prevent contact with the sample collection area and/or sampling area, prior to analysis. This can also serve to protect these areas post-analysis from damage or from user contact, and prevent the sample substrate from contaminating other objects. For example, it is possible to provide a protective cover which is attached to the housing and contains a flap that lies over the sample collection area to prevent contamination and user contact. The flap, or even the entire cover, can be designed to be automatically lifted upon coupling of the sample card to the reader device and automatically closed when the card is removed from the reader device. In addition, reader device 80 can be designed to update firmware. Allowing the firmware to be updated allows improved algorithms to be uploaded into the system for data analysis (signal processing, lighting conditions, drying/heating procedure, etc.). As new sample cards become available for additional target analytes, firmware upgrades will upload the corresponding algorithms for the new sample cards, thus allowing existing hardware to be used for the new capabilities. Furthermore, the reader device may also have wireless capability for image transfer, as well as remote logins for diagnostic work. USB will also allow logins for diagnostic work and could eventually become an interface to a smart interface to extract forensic information. Finally, the reader device can contain an ambient light sensor, particularly to sense if there is stray light in the device which would warrant an adjustment in lighting parameters for consistent performance.

We claim:

1. An analyte detection system comprising:
    a. a sample card including:
        a housing having at least one cavity made from a flexible material,
        a sample substrate, at least a portion of the sample substrate onto which a sample is to be collected, being configured to be exposed from outside the housing,
        at least one test capsule held in the at least one cavity and containing a liquid to be delivered to a collected sample,
        an absorbent pad to collect the liquid from the at least one test capsule after the liquid is released and to deliver the liquid to the sample substrate,
        one or more detection reagents contained in at least one of the at least one test capsule, the sample substrate, and the absorbent pad, and
        an identifying mark indicating a sample card type; and
    b. a reader device including:
        a housing with a card carrier to receive the sample card,
        a door shiftably mounted relative to the housing and the card carrier between opened and closed positions,
        a card rupture mechanism configured to release the liquid in the test capsule after a sample card has been inserted into the card carrier and the door is subsequently placed in the closed position,
        a light assembly,
        an optical reader configured to: read the identifying mark in indicating the sample card type such that the system conducts an analysis protocol for an analyte or group of analytes specific to the sample card type with the analyte or group of analytes being selected from the group consisting of explosives, narcotics, gunshot residue, organophosphate reagents, and toxic industrial chemicals, and read an optical signal produced by reaction of the collected sample and the one or more detection reagents, a signal processor for determining a test result based on the optical signal, and a communication system for conveying the test result.

2. The analyte detection system of claim 1, wherein the sample card contains two test capsules containing different solutions that mix prior to reaching the sample substrate.

3. The analyte detection system of claim 1, wherein the sample card contains two test capsules and two absorbent pads to deliver two liquids to separate portions of the sample substrate, such that two separate analyses can be conducted on different portions of the sample substrate.

4. The analyte detection system of claim 1, wherein the sample card further contains a control area.

5. The analyte detection system of claim 1, wherein the identifying mark is constituted by a bar code, a serial number, a printed graphic or a color coding which is recognizable by the optical reader, or a notch or mechanical key which can be sensed by the reader device.

6. The analyte detection system of claim 1, wherein the sample card further contains a card cover to prevent contact with the sample substrate before sample collection and after analysis.

7. The analyte detection system of claim 1, wherein the reader device further contains at least one of a heater, a drying fan, a temperature sensor, a humidity sensor, and an ambient light sensor.

8. The analyte detection system of claim 1, further comprising: at least one sensor for detecting that the sample card is coupled to the reader device and the door has assumed the closed position.

9. The analyte detection system of claim 1, wherein the light assembly contains one or more of ultraviolet and white light sources selected from the group consisting of: light emitting diodes, cold cathode fluorescent lamps, and hot cathode fluorescent lamps.

10. The analyte detection system of claim 1, wherein the optical reader comprises a camera for establishing one or more digital images as the optical signal.

11. The analyte detection system of claim 1, wherein the reader device further includes data storage and means to access at least one of remote and local stored records.

12. A method of detecting an analyte comprising:

collecting a sample on a sample substrate exposed to outside of a housing of a sample card having an identifying mark indicating a specific analyte or group of analytes for which the sample card was designed with the analyte or group of analytes being selected from the group consisting of explosives, narcotics, gunshot residue, organophosphate reagents, and toxic industrial chemicals, said sample card containing at least one test capsule held in at least one cavity made from a flexible material of the housing and containing a liquid, and an absorbent pad, wherein at least one of the sample substrate, the at least one test capsule and the absorbent pad contains detection reagents;

coupling the sample card to a card carrier of a reader device by opening a door of the reader device and inserting the sample card into the card carrier of the reader device;

performing a detection cycle including: releasing the liquid by rupturing the at least one test capsule with a card rupture mechanism of the reader device by applying pressure to the at least one test capsule after the sample card has been inserted into the card carrier and the door is subsequently placed in the closed position, whereby the liquid dissolves the detection reagents contained in the sample card and delivers said reagents to the sample, causing a chemical reaction between the sample and the detection reagents to occur; reading an identifying mark on the sample card and conducting an analysis protocol specific to the sample card; and assessing an optical signal produced by the chemical reaction of the sample and the detection reagents in establishing a test result; and communicating the test result.

13. The method of claim 12, wherein coupling the sample card to the reader device is accomplished by inserting the sample card into the card carrier which is disposed between a housing and a door of the reader device.

14. The method of claim 13, wherein the detection cycle is automatically initiated upon the reader device sensing that the sample card is coupled to the card carrier and the door is subsequently closed.

15. The method of claim 12, wherein assessing the optical signal includes processing one or more digital images recorded from an optical unit within the reader device over a specified period of time and/or analyzing one or more of a control area or calibration area present on the sample card.

16. The method of claim 12, wherein assessing the optical signal and establishing the test result includes assessing one or more attributes including color component identification, color component separation, signal energy levels, relationships between color components, time domain appearance and disappearance of signals, signal shape, and signal distinction.

17. The method of claim 12, wherein:

if the analyte is explosive-related comprising one or more of nitramine, organic nitrate and inorganic nitrate compounds and compounds containing the same, including RDX, HMX, C4, PETN, Semtex, EDGN, nitroglycerin, nitrocellulose, ammonium nitrate, ANFO, urea nitrate, and potassium nitrate, using an acid, one or more organic amines, and a reducing agent as the at least one detection reagent; or if the analyte is an explosive comprising one or more of peroxide-, chlorate-, and bromate-containing explosives, using an azino-containing compound as the at least one detection reagent.

18. The method of claim 12, wherein:

if the analyte is a narcotic comprising amphetamine-like compounds, using a pyrylium compound as the at least one detection reagent;

if the analyte is a narcotic which is opiate-based, using cis-aconitic anhydride as the at least one detection reagent; or if the analyte is a narcotic comprising one or more of cocaine- and PCP-based narcotics, using a mixture of a cobalt(II) salt and a pyrylium salt as the at least one detection reagent.

* * * * *